United States Patent [19]
Suffis et al.

[11] Patent Number: 4,477,431
[45] Date of Patent: Oct. 16, 1984

[54] COSMETIC COMPOSITION CONTAINING HIGH LEVELS OF POWDER

[75] Inventors: Robert Suffis, Randolph; Myron Barchas, Montclair, both of N.J.

[73] Assignee: The Mennen Company, Morristown, N.J.

[21] Appl. No.: 225,005

[22] Filed: Jan. 14, 1981

[51] Int. Cl.³ .......................... A61K 7/34; A61K 7/38; A61K 7/035
[52] U.S. Cl. ..................... 424/66; 252/309; 424/68; 424/69; 424/73; 424/184; 424/357
[58] Field of Search ........................ 424/65, 66, 68, 69, 424/184; 252/309, 312

[56] References Cited

U.S. PATENT DOCUMENTS

| 2,002,829 | 5/1935 | Osterberg . | |
| 2,523,316 | 9/1950 | McClenahan et al. . | |
| 3,300,387 | 1/1967 | Kole . | |
| 3,792,158 | 2/1974 | Fein et al. | 424/66 |
| 3,852,475 | 12/1974 | Tarangul . | |
| 3,998,788 | 12/1976 | Rubino | 424/66 |
| 4,010,252 | 3/1977 | Hewit | 424/67 |
| 4,049,792 | 9/1977 | Elsnau | 424/DIG. 5 |
| 4,053,581 | 10/1977 | Pader et al. | 424/66 |
| 4,065,564 | 12/1977 | Miles, Jr. et al. | 424/66 |
| 4,110,427 | 8/1978 | Kalat | 424/66 |
| 4,151,272 | 4/1979 | Geary et al. | 424/DIG. 5 |
| 4,229,432 | 10/1980 | Geria | 424/68 |
| 4,268,499 | 5/1981 | Keil | 424/66 |
| 4,280,994 | 7/1981 | Turney | 424/67 |

FOREIGN PATENT DOCUMENTS

| 2301829 | 1/1973 | Fed. Rep. of Germany | 424/65 |
| 11163826 | 5/1958 | France | 424/68 |
| 61239 | 5/1977 | Japan | 424/66 |
| 2018590 | 10/1979 | United Kingdom | 424/66 |

OTHER PUBLICATIONS

Cosmetics and Perfumery, 12/1974, Kahn et al.

Primary Examiner—Dale R. Ore
Attorney, Agent, or Firm—Davis Hoxie Faithfull & Hapgood

[57] ABSTRACT

The invention is directed to a cosmetic product comprising a powder/oil dispersion having high levels of cosmetic powder. More particularly, it is directed to an antiperspirant where at least part of the powder content is an astringent, such as aluminum chlorhydrate. By using one or more cationic or nonionic surfactants in an oily vehicle, a highly concentrated, stable dispersion having relatively low viscosity and creamy consistency, with a dry, non-oily feel is obtained.

9 Claims, No Drawings

COSMETIC COMPOSITION CONTAINING HIGH LEVELS OF POWDER

This invention is directed to a viscous, flowable cosmetic product, such, for example, as an antiperspirant, suitable for application to the body by hand or by any of various styles of applicator and characterized by a very high solids/liquid ratio. More particularly, it is directed to an oil-based dispersion containing a high level of cosmetically active power. In a preferred species of the invention, some or all of the powder may be an astringent, such as aluminum chlorhydrate or zirconium chlorhydrate, which are useful antiperspirants.

Anhydrous mixtures of powders and oils in which the powder comprises as much as 50% by weight of the total product are usually crumbly, claylike and not flowable or spreadable. In accordance with the present invention, these physical imperfections are avoided and a product is obtained having extremely high solids content but with a viscosity similar to that of a cosmetic lotion or cream, with a dry, smooth feel, low tack, and little or no oiliness or powder fall out. It can be applied by means of various dispensing devices such as push-up type applicators.

In accordance with the invention, these properties are obtained by means of a cosmetic product comprising a dispersion in oil of a powdered cosmetic solid, said dispersion comprising from about 35 to about 70% by weight of said cosmetic solid, from about 1 to about 20% by weight of an inorganic gelling agent, from about 1 to about 10% by weight of a surfactant and from about 19 to about 45% by weight of a cosmetically acceptable oil, said surfactant comprising nonionic or cationic surface active ingredients or a mixture of the two types. Various othe components, such as perfumes, colorants, stabilizers, emollients and the like, may be present in minor amounts, for example, in proportions of 1% or less by weight.

Despite their high solids loading, which permits application of very small amounts of product while still delivering effective levels of active ingredients, compositions according to the invention retain a rheology which makes their use convenient in various cosmetic applications, such as antiperspirants, protective creams and lotions, foot products, after-shave lotions and pre-electric shave products.

The cosmetic powder employed in compositions of the invention may be antiperspirant, such as a microfine grade of aluminum chlorhydrate or zirconium chlorhydrate, or an entirely different powder, such as starch, corn starch, talc or kaolin, or it may be mixtures of each of these types. Preferably the antiperspirant powder has a particle size range between about 8 and 13 microns, with 95% of its particles below 10 microns. Observance of these ranges optimizes the physical characteristics such as the dry feel and matte appearance of the product.

Inorganic gelling agents which are useful in the present invention comprise, typically, reaction products of a clay, such as montmorillonite or bentonite, with quaternary ammonium salts which conform generally to the formula

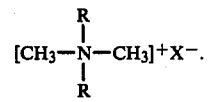

In this formula, R represents any hydrogenated tallow fatty radical, preferably of 10 to 30 carbon atoms, and X represents halogen, preferably chlorine.

The gelling agent of choice is a composition comprising about 15% of the rection product of hectorite with dimethyl distearyl ammonium chloride, about 10% propylene carbonate and about 75% isopropyl myristate. This gelling agent is available commercially from National Lead Indiana as Bentone IPM-VS gel. Hectorite is one of the montmorillonite minerals which are the principal constituents of bentonite clay.

Other useful gelling agents include fumed silicon dioxide, available from Cabot Corporation as Cab-O-Sil, and syloid silicas, which are reaction products of sodium silicate and sulfuric acid.

It has now been found that where a clay-quaternary ammonium salt reaction product is used as the gelling agent, the gelling agent preferably comprises about 5 to about 20% of total product. Where fumed silicon dioxide is used as the gelling agent, it preferably comprises about 1 to about 7% of total product.

The surfactants used in the present invention are important in enabling high solids levels to be obtained. Useful surfactants include nonionic and cationic surface active ingredients either alone or in combination. Preferred nonionic surfactants are polyalkylene oxide modified long chain fatty alcohols and esters, such as polyoxyethylene (2) oleyl ether (sold as Brij 93 by ICI United States, Inc., hereafter "ICI") and polyoxyethylene (20) sorbitan trioleate (sold as Tween 85 by ICI). Suitable alternatives for these surfactants are, respectively, polyoxyethylene (10) oleyl ether (sold as Brij 97 by ICI) and polyoxyethylene (4) sorbitan monostearate (sold as Tween 61 by ICI). (The parenthetical number in the chemical name refers to the degree of ethoxylation of the compound.) Other useful nonionic surfactants include polyoxyethylene derivatives of propylene glycol stearate, lauryl ether, cetyl ether, stearyl ether, oleyl ether, stearate, sorbitan monopalmitate, sorbitan monostearate, sorbitan monooleate and the like.

The cationic surfactant is preferably a quaternary ammonium compound having a long chain alkyl group attached to the nitrogen atom. The cationic surfactant of choice is dimethyl lauramine oleate, sold as Necon LO Cationic by Alzo Inc. of New Jersey. Other suitable cationic surfactants include substituted pyridinium halides, such as N-(stearoyl colaminoformylmethyl) pyridinium chloride or cetyl pyridinium chloride, N-soya-N-ethyl morpholinium ethosulfate, alkyl dimethyl benzyl ammonium chloride, (diisobutyl phenoxy ethoxy) ethyl dimethyl benzyl ammonium chloride, and the like.

The combination of one or more nonionic surfactant ingredients with one or more cationic surfactant ingredients is preferred. However, it should be understood that nonionic surfactants or cationic surfactants may each be used without the other.

"Cosmetically acceptable oils" are those customarity used in cosmetic applications and include mineral oil (viscosity of about 48 to 365 saybolt seconds universal), caprylic/capric triglyceride (viscosity of about 20 to 30 cps. at 25° C.), propylene glycol dicaprylate/dicaprate (about 9 cps. at 25° C.), hybrid safflower oil (about 70 cps. at 25° C.), isopropyl myristate (about 8 cps. at 25° C.), isopropyl palmitate (about 10 cps. at 25° C.), fuly methylated linear (about 0.65 to 60.0 cst.) and cyclic (about 2.5 to 4.0 cst.) polysiloxanes, propoxylated myristyl and stearyl alcohol, vegetable oils such as corn oil, cottonseed oil, coconut oil, castor oil, and the like. A water insoluble mineral oil, such as that described above, is preferred.

The products of the invention can be prepared by mixing the inorganic gelling agent, oil and surfactant at room temperature, using a suitable mixer, until the mixture is smooth. The cosmetic powder is then added while vigorous stirring is continued. Perfume, colorants, etc., if used, may then be added. Stirring should be continued until the mixture is free of agglomerates.

The invention of the present application has been found to be particulary useful for antiperspirant formulations, such as those set forth below in Table A. Formulation 1 describes an anhydrous antiperspirant having a very high level of active powder, i.e., Micro Dry, M.S., while Formulations 2 and 3 describe anhydrous antiperspirants with more usual levels of antiperspirant, but containing very high total cosmetic powder levels. All percentages are by weight of total product.

TABLE A

| Ingredient | Formulation 1 | 2 | 3 |
|---|---|---|---|
| Micro Dry, M.S. | 60.1% | — | — |
| Astringen 10 | — | 22.0% | 22.6% |
| Mineral Oil | 24.5 | 37.1 | 43.6 |
| Necon LO Cationic | 0.3 | 0.2 | — |
| Perfume | — | 1.0 | — |
| Brij 30SP | — | — | 0.7 |
| Brij 93 | 2.5 | — | — |
| Tween 85 | 2.1 | 1.42 | — |
| Bentone IPM-VS Gel | 10.5 | 17.64 | — |
| Cab-O-Sil | — | — | 4.1 |
| Purity 826 Starch | — | 20.64 | — |
| Corn Starch | — | — | 29.0 |

Micro Dry, M.S. and Astringen 10 are both aluminum chlorhydrate, microfine grade. Purity 826 starch is a pharmaceutical grade of starch. The corn starch used in Formulation 3 is food grade, refined corn starch. Brij 30SP is a nonionic surfactant, polyoxyethylene (4) lauryl ether, sold by ICI. The other ingredients have been previously described.

In preparing the products of Table A, the inorganic gelling agent, oil and surfactant were mixed at room temperature in a suitable mixer until the mixture was smooth and free of agglomerates. Next, the cosmetic powder was added while the mixture was stirred vigorously. In Formulation 2, the perfume was then added. Stirring was continued until the mixture was smooth.

The present invention makes possible a totally anydrous antiperspirant in which the active ingredient is carried in a non-aqueous base, such as mineral oil or silicone oil. Because of the small amount of total product which is needed for effective antiperspirant protection, the non-aqueous base is not present in sufficient amounts to cause undesirable cosmetic effects, such as greasy feel or appearance. The invention makes high powder loadings practical by providing a workable viscosity and stable rheology and eliminates the need to use such devices as roller mills to aid in dispersing the powders.

Another advantage to the compositions of the present invention is that they can be applied as lotions or creams, but assume the appearance and feel of a powder within seconds after application.

What is claimed:

1. A viscous, flowable, non-alcoholic, anhydrous cosmetic composition consisting essentially of, by weight of total product, about 35 to about 70% cosmetic powder, about 1 to about 20% inorganic gelling agent, about 1 to about 10% surfactant selected from the group consisting of nonionic, cationic and mixtures thereof and about 19 to about 45% cosmetically acceptable oil.

2. The cosmetic composition of claim 1 wherein the cosmetic powder comprises aluminum chlorhydrate or zirconium chlorhydrate.

3. The cosmetic composition of claim 2 wherein the inorganic gelling agent comprises about 15% of the reaction product of a clay with a quaternary ammonium salt of the formula

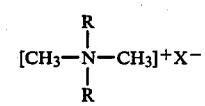

wherein R is any hydrogenated tallow fatty radical having 10 to 30 carbon atoms and X is any halogen, about 10% propylene carbonate and about 75% isopropyl myristate.

4. The cosmetic composition of claim 3 wherein the inorganic gelling agent comprises the reaction product of bentonite clay and dimethyl distearyl ammonium chloride.

5. The cosmetic composition of claim 2 wherein the inorganic gelling agent is fumed silicon dioxide.

6. The cosmetic composition of claim 5 wherein the inorganic gelling agent comprises about 1 to about 7% of total product.

7. The cosmetic composition of claim 4 wherein the surfactant comprises a mixture of nonionic and cationic ingredients, one or more nonionic surfactant ingredients being chosen from the group consisting of polyoxyethylene (2) oleyl ether, polyoxyethylene (20) sorbitan trioleate and polyoxyethylene (4) sorbitan monostearate and the cationic surfactant ingredient being dimethyl lauramine oleate.

8. The cosmetic composition of claim 6 or 7 wherein the oil is mineral oil.

9. The cosmetic composition of claim 6 wherein the surfactant is polyoxyethylene (4) lauryl ether and the oil is mineral oil.

* * * * *